US006669639B1

(12) United States Patent
Miller et al.

(10) Patent No.: US 6,669,639 B1
(45) Date of Patent: Dec. 30, 2003

(54) ULTRASONIC DIAGNOSTIC IMAGING SYSTEM WITH ARTICULATING DISPLAY

(75) Inventors: Brad A. Miller, Bothell, WA (US); John R. Murkowski, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/267,173

(22) Filed: Oct. 8, 2002

(51) Int. Cl.⁷ .................................................. A61B 8/00
(52) U.S. Cl. ...................................................... 600/443
(58) Field of Search .................................. 600/447, 443, 600/437; 60/448; 73/625, 626

(56) References Cited

U.S. PATENT DOCUMENTS

| | | | |
|---|---|---|---|
| 4,625,731 A | * 12/1986 | Quedens et al. | ............ 600/443 |
| D300,241 S | 3/1989 | LaCelle et al. | |
| 5,129,397 A | * 7/1992 | Jingu et al. | ................. 600/437 |
| D340,770 S | 10/1993 | Ohnuma et al. | |
| 5,251,631 A | 10/1993 | Tsuchiko et al. | |
| D352,106 S | 11/1994 | Fanney et al. | |
| D398,059 S | 9/1998 | Kwak | |
| 5,924,988 A | 7/1999 | Burris et al. | |
| 5,941,824 A | 8/1999 | Hwang | |
| 6,241,673 B1 | * 6/2001 | Williams | .................... 600/437 |
| 6,544,179 B1 | * 4/2003 | Schmiesing et al. | ........ 600/447 |

* cited by examiner

*Primary Examiner*—Francis J. Jaworski
*Assistant Examiner*—Maulin Patel
(74) *Attorney, Agent, or Firm*—W. Brinton Yorks, Jr.

(57) ABSTRACT

An ultrasonic diagnostic imaging system cart is provided with an articulation mechanism for the image display. The articulation mechanism is pivotally mounted to the cart and to the display and includes an intermediate pivot elbow which allows the display to be moved laterally and forward and back from its nominal home position. One arm of the articulating mechanism is inclined to allow the display to clear other components of the cart when articulated and to prevent the development of pinch points. One of the joints of the articulating mechanism includes a locking device which selectively locks the joint to alter the articulation characteristic of the mechanism.

16 Claims, 5 Drawing Sheets ns and, in particular, to ultrasonic diagnostic imaging
ULTRASONIC DIAGNOSTIC IMAGING SYSTEM WITH ARTICULATING DISPLAY This invention relates to ultrasonic diagnostic imaging systems and, in particular, to ultrasonic diagnostic imaging systems with displays that can be articulated for ease and comfort of viewing.

Designs of ultrasound systems are increasingly taking the comfort and convenience of the user and patient into consideration. These efforts have been stimulated by reports of repetitive stress injuries and by the desire to provide additional comfort and convenience for those using the ultrasound system, including both the operator and the patient. One component of the ultrasound system which is amenable to such designs is the display device on which the diagnostic image is displayed. As the operator is guiding the ultrasound probe over the body of the patient to acquire the anatomy of interest in the field of view of the probe, the operator is constantly watching the image produced by the probe on the system display. To do this comfortably and effectively, the operator needs to position the patient, the operator, and the display in related positions that enable the anatomy of interest to be effectively scanned while the operator watches the ultrasound image on the display. This procedure is aided when the display device, which may be a CRT monitor or a flat-panel display, can be easily moved to the desired viewing position.

To enable the user to adjust the monitor position, some ultrasound systems mount the monitor on the articulation mechanism conventionally found on many computer monitors. These mechanisms include a base mount on which the monitor can swivel about a vertical pivot axis, and which permits the monitor to be rocked about a horizontal axis so as to face more upward or downward toward the operator. It is desirable to facilitate more than just these basic movements, so that the display will have a broader range of movements and to accommodate both the viewing position for the scanning clinician and a viewing position for the patient.

In accordance with the principles of the present invention, a cart-borne ultrasound system includes an articulating mounting device for the image display. In a preferred embodiment the articulation device has three pivot axes about which the sections of the device can be rotated to provide a wide range of movement. The range of motion is restricted from at least one position where the monitor would interfere with other parts of the system. In the preferred embodiment the articulating mount includes an inclined section which enables the display to clear other parts of the system when being moved, and which prevents the development of a pinch point in the articulating device.

Figure 1:
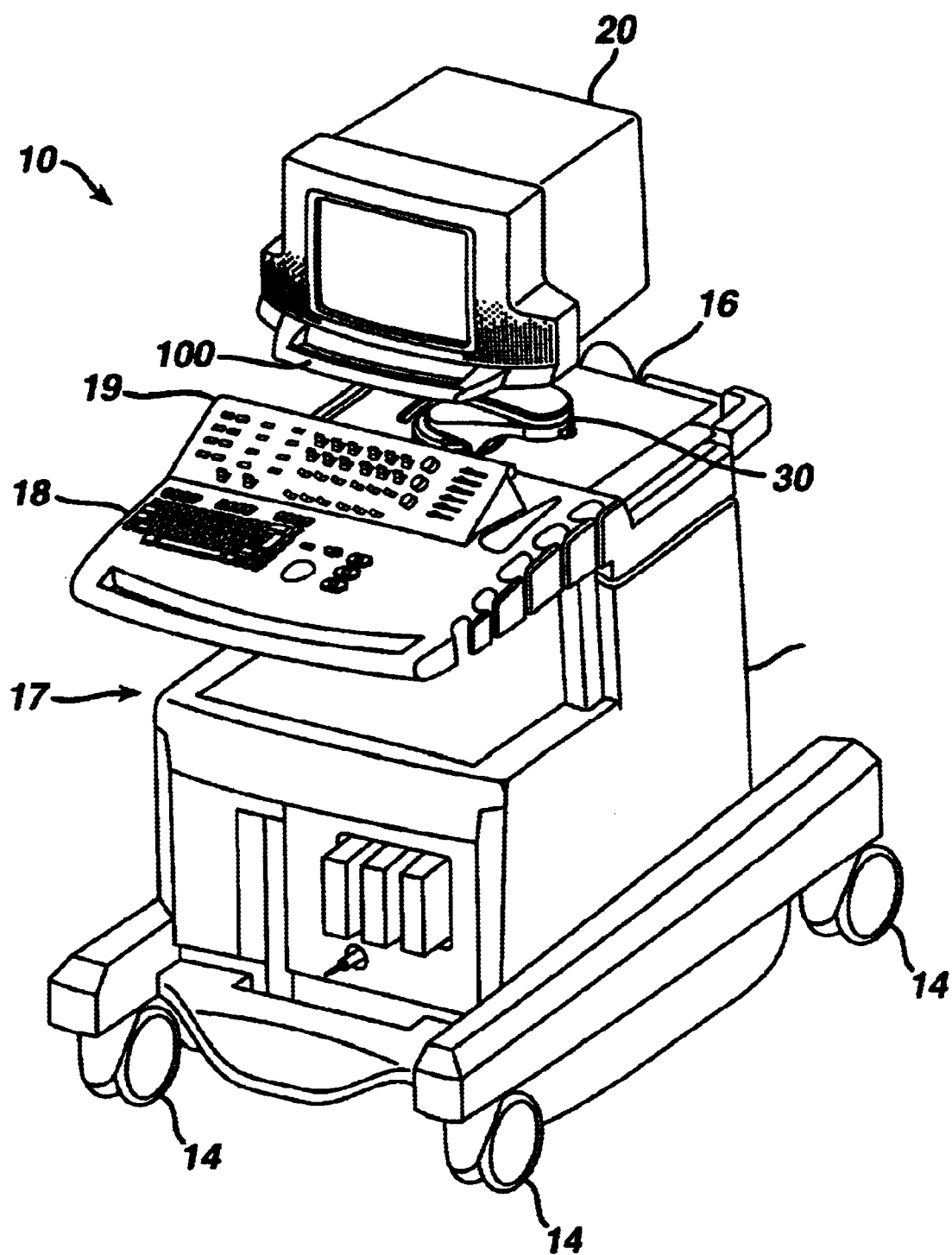
FIG. 1 illustrates a cart-borne ultrasound system of the present invention in a forward perspective view.
Figure 2:
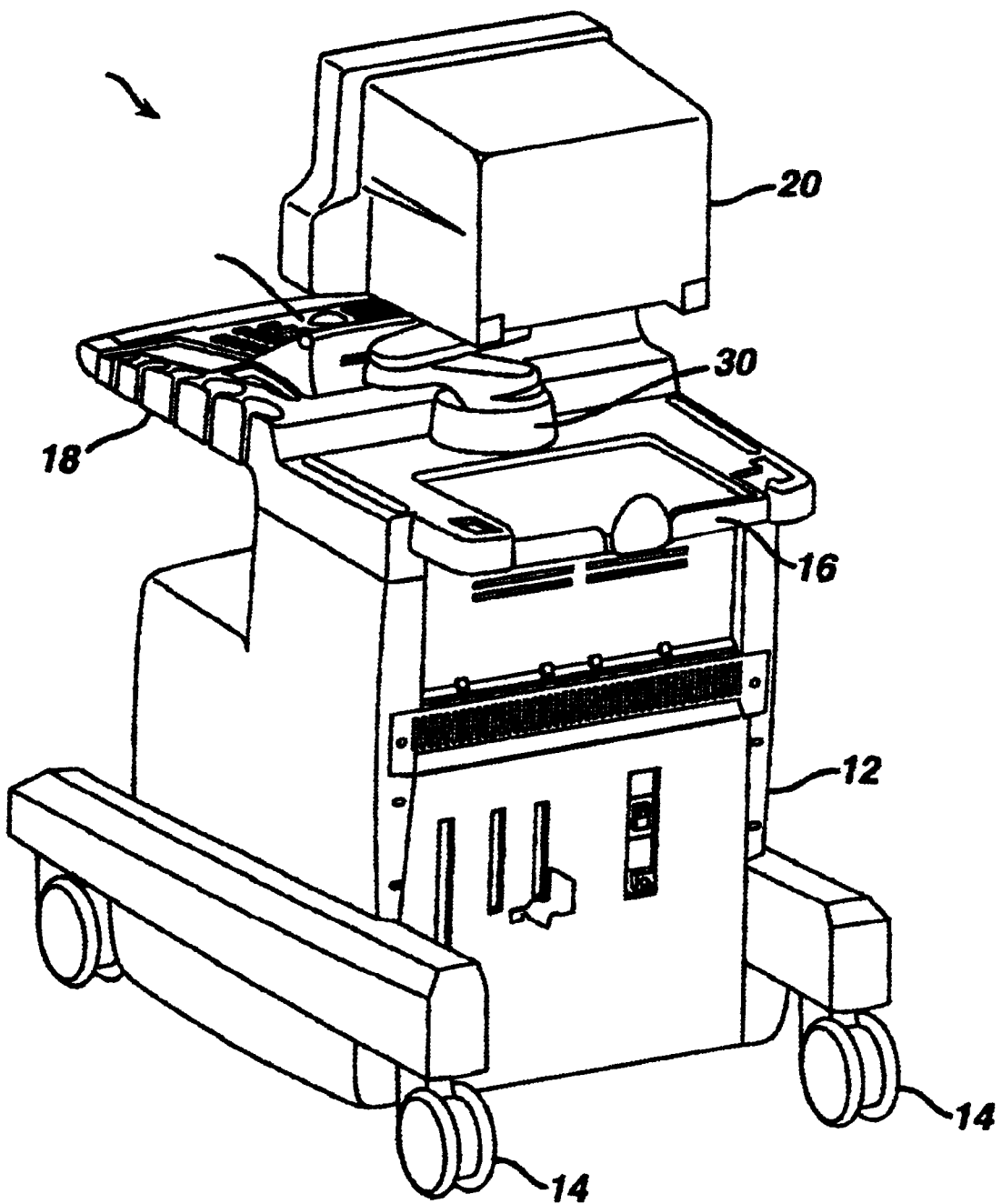
FIG. 2 illustrates a cart-borne ultrasound system of the present invention in a rearward perspective view.

Referring first to FIGS. 1 and 2, a cart-borne ultrasound system 10 is shown in forward and rearward perspective views. The ultrasound system cart includes a main body 12 which contains the electronics of the system, including a card cage with specially designed ultrasound circuitry such as beamformers and signal and image processors and associated power supplies. The cart is mounted on wheels or casters 14. The cart has a top surface in the front which forms an accessory bay 17 in which accessory devices such as a printer can be installed. Above the accessory bay 17 is a control panel 18 which the operator uses to set up and control an ultrasound examination. The illustrated control panel has a rear portion 19 which is inclined upward so as to put the buttons and switches on that portion of the control panel within easy reach of the operator. In a preferred embodiment the control panel is movable so that it can be raised and lowered and be more comfortable for both sitting and standing operators.

The cart also has a rear top surface 16 which accommodates other accessory devices such as a video recorder.

In accordance with the principles of the present invention the ultrasound system 10 has a monitor 20 located above the control panel. The monitor 20 is mounted on an articulating mechanism 30 which allows the monitor to be rotated and moved to a comfortable viewing position for the operator and/or the patient. The ultrasound system display may alternatively comprise a flat panel LCD or plasma display instead of the CRT monitor shown in FIGS. 1 and 2. The articulating mechanism 30 allows the monitor to be swiveled and repositioned without striking the raised portion 19 of the control panel or any accessory device located on the rear surface 16 of the cart.

Figure 3:
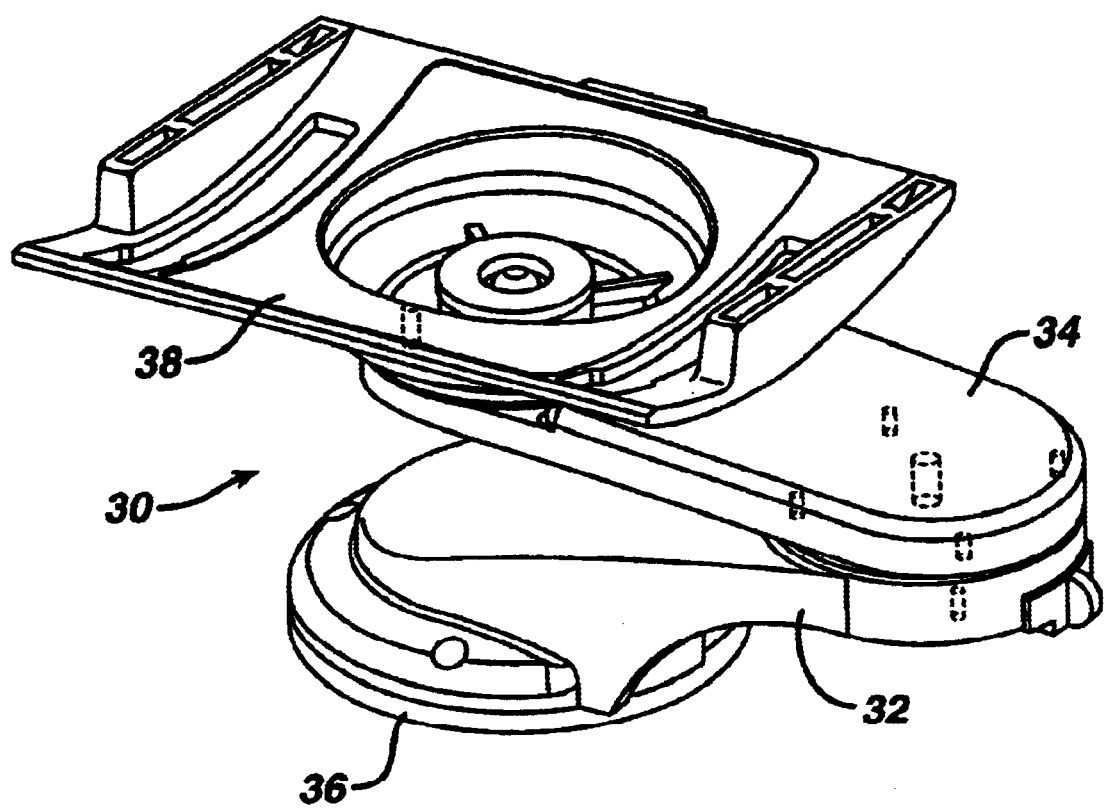
FIG. 3 is a perspective view of an articulating display mount constructed in accordance with the principles of the present invention.

The display articulating mechanism 30 is shown in an enlarged perspective view in FIG. 3. The embodiment there shown has a mount plate 36 at the bottom which can be secured to the top of the ultrasound system cart as described below. The mechanism 30 has a lower articulation arm 32 which is pivotally mounted on the mount plate 36. The lower articulation arm is a rigid member which is inclined upward at approximately a 16° angle which enables the articulating mechanism and display device to clear the raised portion 19 of the control panel 18 when the control panel is fully elevated and the monitor 20 is rotated forward over the control panel. In a constructed embodiment the lower arm provides an elevation of approximately three inches above the top surface of the cart. At its upper end the lower articulation arm 32 is pivotally connected to an upper articulation arm 34. At its other end the upper articulation arm 34 is pivotally connected to a monitor tilt and swivel base 38. The inclined angle of the lower articulation arm also prevents development of a pinch point between the lower arm and the top surface of the cart and between the lower and upper arms when the two arms overlap, which would not be the case if the arms were flush with each other or the lower arm were flush with the surface of the cart. The mount plate, lower articulation arm, and upper articulation arm can be hollow members which enable the passage of a power cord and cable to pass from the main body of the ultrasound system cart, through the pivot joints and arms, and to a monitor or flat panel display located on the tilt and swivel base. Alternatively the cord and cable can be loosely located about the articulating mechanism to enable the display to articulate freely without binding or tangling the cord and cable.

Figure 4:
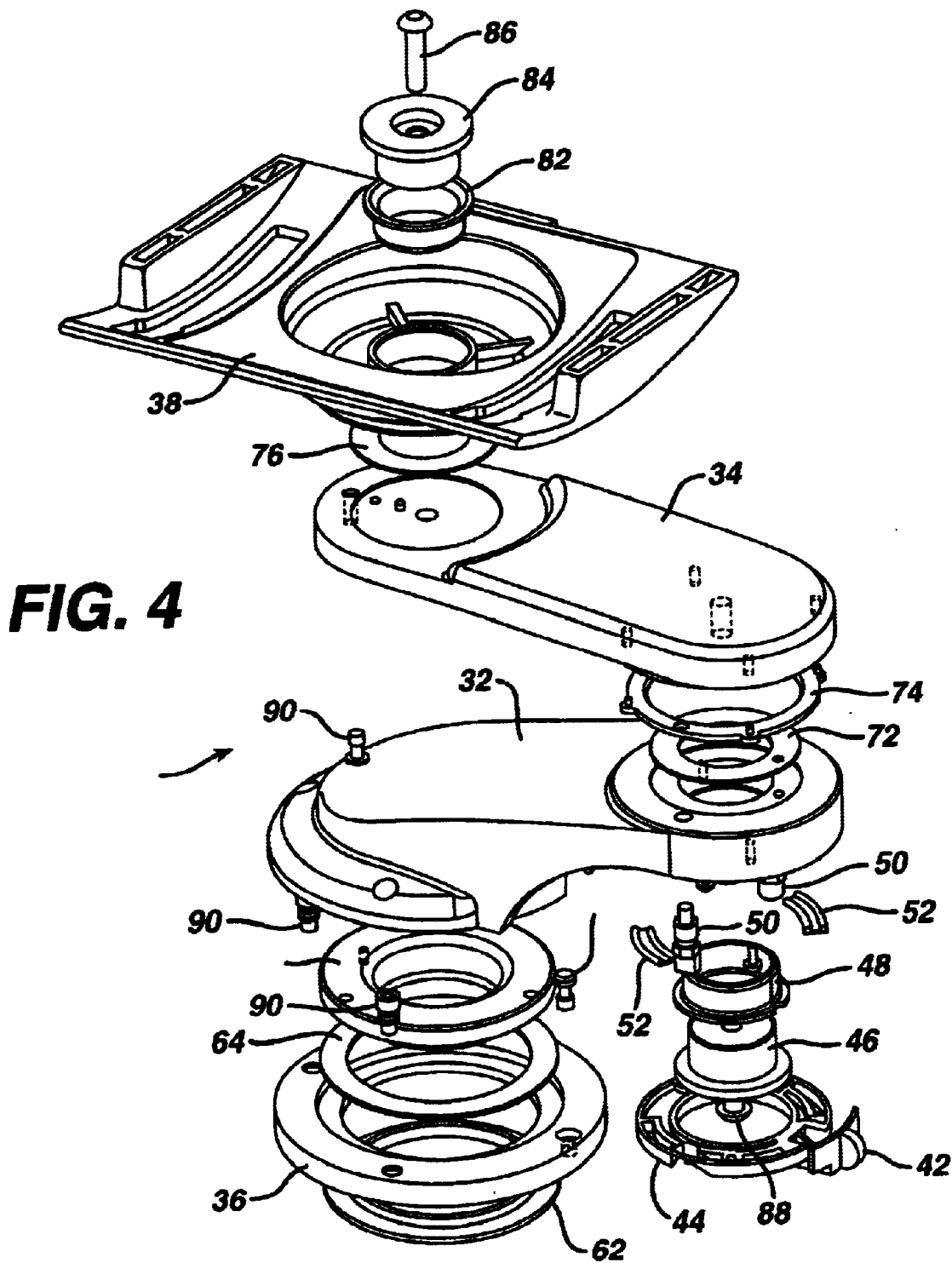
FIG. 4 is an exploded perspective view of the articulating display mount of FIG. 3.

FIG. 4 is an exploded view of the articulating mechanism 30. The mount plate 36 is sandwiched by two bearing washers 62 and 64 which are conventional bearing washers with smooth Teflon® like surfaces. Compression of the mount plate and bearing washers is maintained by a retainer 66, which is mounted to the top of the ultrasound system cart. The lower articulation arm 32 is mounted by bolts 90 to the mount plate 36. When the lower articulation arm is pivoted relative to the cart, the mount plate rotates between the bearing washers 62 and 64, with the retainer 66 preloading the clamping force (rotational friction) of this lower joint of the articulating mechanism 30.

The mount plate 36 has a screw 37 extending downward from the mount plate which travels in a circular trough formed in the top surface of the cart. The length of this trough defines a range of movement and end stops which restrict the travel of the screw 37 and thereby the angle of rotation of the lower joint to a predetermined angle. In a constructed embodiment the range of rotation used is 210°, which does not allow the lower articulation arm 32 to swing over the front-most 150° of a full circular range of rotation. This choice of pivot range prevents the lower articulation arm to swing fully to the front of the system where it might otherwise impact the upper portion 19 of the control panel. The lower articulation arm 32 is allowed to swing completely over the rear surface 16 of the cart, where the upward inclination of the arm enables it to clear an accessory device located on the rear surface 16.

The upper and lower articulation arms are connected together by an elbow joint. The elbow joint includes a bearing shaft 46 riding in a flanged bearing 48 and connected by a bolt 88 to the upper articulation arm 34. Rotation of the elbow joint is facilitated by a thrust washer 72 having a lubrication surface and located between the lower and upper articulation arms. In a constructed embodiment the elbow joint is allowed to turn freely but has two detent positions in which the joint can be locked in a fixed position. This is provided by a locking mechanism, including a lock release mechanism 44 with a lock button 42, a pair of spring-loaded lock pins 50, and a pair of spring retainers 52 which retain two springs (not shown) in the locking mechanism. Whenever the articulation arms are oriented parallel to each over in an overlapping position, or parallel to each other and in an extended position, the two lock pins 50 snap into holes in the upper articulation arm 34, locking the two arms in position. To release this locking mechanism the lock button 42 is pushed to rotate the lock release mechanism 44 against the force of the two springs. As the lock release mechanism rotates a cammed surface pulls the lock pins downward and out of engagement with the upper articulation arm. The elbow joint can again turn freely until one of the detent positions are engaged again. This mechanism allows the articulating mechanism to be operated as either a three-pivot mechanism or a two-pivot mechanism, at the option of the user. When the elbow is locked to operate the articulation mechanism as a two-pivot mechanism, it can form either a mechanism with both pivot axes aligned (if the arms are of the same length) and centrally located over the cart, or with the pivot axes as widely spaced as possible and the display in a fully extended position. When locked with the two articulation arms aligned and overlapping, the monitor can be located in its nominal "home" position with the display screen facing forward and the elbow extending directly to the rear of the cart. The weight of the monitor is then centered above the center of the cart, where it should be when the cart is being moved. It will be appreciated that a locking mechanism could be located at two or three of the pivot joints of the articulating mechanism to lock several or all of the joints when the cart is being moved or transported.

At the other end of the upper articulation arm 34 the monitor tilt and swivel base 38 is pivotally mounted to the upper arm by a similar flanged bearing 82, bearing shaft 84 and bolt 86. A thrust washer 76 is located between the joint surfaces of the base 38 and the arm 34. This joint is not allowed to rotate continuously as is the elbow joint, but is only permitted to turn in one circle of approximately 360°. In a constructed embodiment a pin extends upward from the upper arm 34 and engages a circular trough formed in the die-cast monitor base 38. This pin and trough allow the monitor to turn 80° in one direction from its nominal forward position and 270° in the other direction, for a total pivotal rotation of approximately 350°. This restriction on continuous rotation prevents the display cables and cords inside the arms from becoming overly twisted due to continuous pivoting of the monitor 20.

The monitor base 38 is seen to be formed to enable the monitor to rock upward and downward in the same manner as a conventional computer monitor base mount.

In a constructed embodiment the monitor can be moved laterally to the left and right of its nominal center position by 11 inches in each direction. The articulation mechanism in that embodiment also enables the monitor to be moved forward 7 inches and rearward 11 inches.

Figure 5:
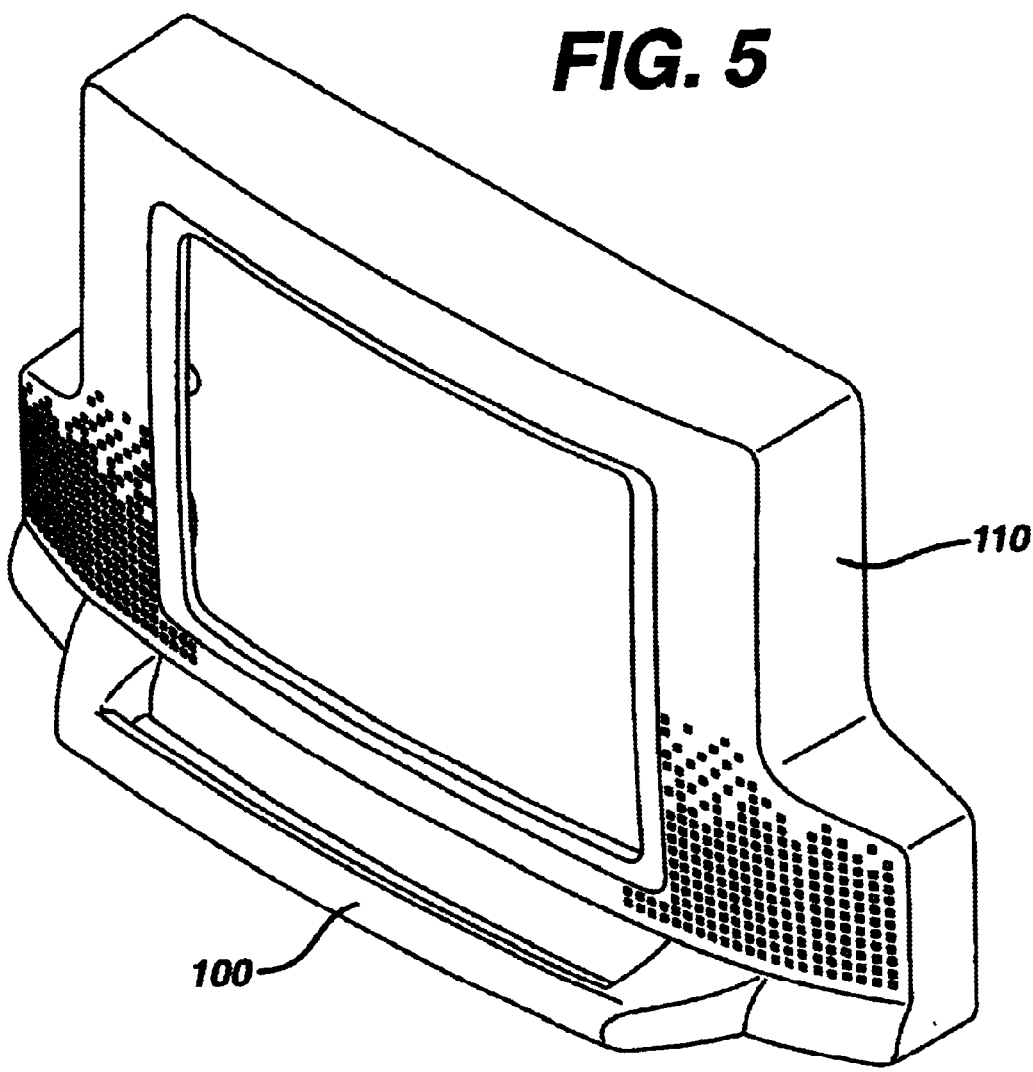
FIG. 5 is a perspective view of a display bezel for a preferred embodiment of the present invention.
Figure 6:
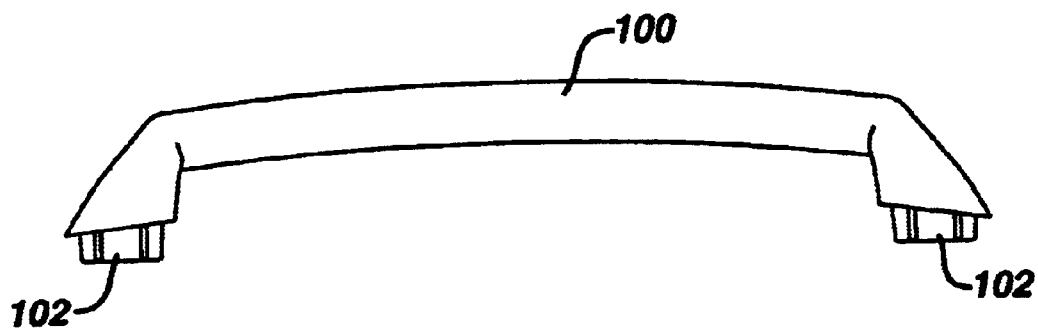
FIG. 6 is a plan view of the display handle used on the display bezel of FIG. 5.

To enable the user to easily move the display device to a different position with one hand, a handle 100 is provided on the front of the display. The handle can be either formed as a part of or attached to the display bezel 110 as shown in FIG. 5. The handle 100 is shown in a plan view in FIG. 6. When the handle 100 is formed as a separate part from the display case or bezel 110, it is preferably formed as a hollow molded part of the same material and color as the display case or bezel. In a constructed embodiment the handle is formed from an ABS plastic material. In a preferred embodiment the handle is attached to the front of display both mechanically and adhesively. In a constructed embodiment the handle is bolted to the bezel from the inside of the bezel and is also bonded to the bezel with a urethane adhesive.

In use the operator can grab the handle with one hand and move or pivot the monitor easily with one hand to a different viewing position. The front handle has been found to be the preferred position for the handle for swiveling the monitor, moving it from side to side or front to rear, and rocking the monitor to face upward or downward.

What is claimed is:

1. An ultrasonic diagnostic imaging system comprising:

a cart in which electronic components of the system are located and having an upper surface;

a control panel mounted on the cart;

an articulating mechanism mounted on the upper surface of the cart which has a lower articulation arm pivotally mounted at a bottom end to the cart and a top end providing a constant inclination above the cart, and an upper articulation arm pivotally mounted at one end to the top end of the lower arm and having a second end; and a display device pivotally mounted at the second end of the upper articulation arm, the articulating mechanism enabling horizontal translation of the display device which is independent of motion of the control panel.

2. The ultrasonic diagnostic imaging system of claim 1, wherein the cart further comprises components which may extend above the level of the upper surface, wherein the inclination of the articulating mechanism is sufficient to enable the display device to be articulated above components extending above the level of the upper surface.

3. The ultrasonic diagnostic imaging system of claim 1, wherein the lower articulation arm is connected to the cart at a lower pivot joint; the lower articulation arm is pivotally connected to the upper articulation arm at an elbow joint; and the second end is connected to the display device at an upper pivot joint, wherein the inclination of the lower articulation arm prevents development of a pinch point between the lower and upper articulation arms.

4. The ultrasonic diagnostic imaging system of claim 3, wherein the pivot joints and the elbow joint further comprise joints which pivot about vertical axes.

5. The ultrasonic diagnostic imaging system of claim 4, wherein at least one of the joints includes a pivot restrictor which restricts the range of pivoting of the joint to less than 360°.

6. The ultrasonic diagnostic imaging system of claim 5, wherein the pivot restrictor of at least one of the joints comprises means for preventing collision of the articulating mechanism and display device with another component of the ultrasound system.

7. The ultrasonic diagnostic imaging system of claim 5, wherein one of the joints includes a pivot restrictor which restricts the range of pivoting to substantially 360°; one of the joints includes a pivot restrictor which restricts the range of pivoting to less than 360°, and one of the joints permits pivoting in excess of 360°.

8. The ultrasonic diagnostic imaging system of claim 1, wherein the display device comprises a CRT display.

9. The ultrasonic diagnostic imaging system of claim 1, wherein the display device comprises a flat panel display.

10. An ultrasonic diagnostic imaging system comprising:

a cart in which electronic components of the system are located and having an upper surface;

a control panel mounted on the cart;

an articulating mechanism mounted on the upper surface of the cart which has a lower articulation arm connected to the cart at a first articulation joint, and an upper articulation arm connected to the lower arm at a second articulation joint;

a display device connected to the upper articulation arm at a third articulation joint, the articulating mechanism enabling horizontal translation of the display device independent of movement of the control panel; and a locking mechanism, located at one of the articulation joints, which acts to selectively prevent articulation of the joint.

11. The ultrasonic diagnostic imaging system of claim 10, wherein the articulating mechanism comprises an N-joint articulating mechanism when the locking mechanism is not locked, and an (N−1)-joint articulating mechanism when the locking mechanism joints is locked.

12. The ultrasonic diagnostic imaging system of claim 10, wherein the locking mechanism locks an articulation joint in a predetermined articulated position.

13. The ultrasonic diagnostic imaging system of claim 12, wherein the locking mechanism is located at the second articulation joint; and wherein the locking mechanism acts to lock the first and second articulation arms in a predetermined relationship to each other.

14. The ultrasonic diagnostic imaging system of claim 13, wherein the locking mechanism acts to lock the first and second articulation arms in two different predetermined relationships to each other.

15. The ultrasonic diagnostic imaging system of claim 14, wherein the second articulation joint comprises a vertically pivoting joint; and wherein the locking mechanism acts to lock the first and second articulation arms in either a mutually aligned and overlapping relationship or a mutually aligned and extended relationship.

16. The ultrasonic diagnostic imaging system of claim 10, further comprising a second locking mechanism, located at another one of the articulation joints, which acts to selectively prevent articulation of the other articulation joint.

* * * * *